US00PP09593P

United States Patent [19]

Zaiger et al.

[11] Patent Number: Plant 9,593

[45] Date of Patent: Jun. 25, 1996

[54] APRICOT TREE "POPPY"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 460,974

[22] Filed: Jun. 5, 1995

[51] Int. Cl.[6] ..... A01H 5/00

[52] U.S. Cl. ..... Plt./39

[58] Field of Search ..... Plt./39

*Primary Examiner*—James R. Feyrer

[57] ABSTRACT

A new and distinct variety of apricot tree which has the unique combination of outstanding features that are desirable in a new variety:

1. Early maturity of fruit.
2. Fruit with good flavor and eating quality.
3. Heavy and regular production.
4. Fruit with firm flesh, good handling and shipping quality.
5. Vigorous, semi-spreading growth.

1 Drawing Sheet

ORIGIN OF THE VARIETY

The present new and distinct variety of apricot tree was originated by us in our experimental orchard located near Modesto, Calif., as a first generation seedling from a cross between two seedling selections with the field identification numbers 78EB575 and 123GD161. The female parent with the field identification number 78EB575 originated from a group of open pollinated Spring Giant Apricot (U.S. Plant Pat. No. 5,138) seedlings. The pollen parent with the field identification number 123GD161 originated from a group of open pollinated Earlicot Apricot (U.S. Plant Pat. No. 7,198) seedlings. A large number of first generation seedlings were grown and maintained under careful and continual observation by us, during which time one seedling with early maturing fruit and the especially desirable fruit characteristics described above, which is the present variety, was selected for asexual reproduction and commercialization.

ASEXUAL REPRODUCTION OF THE VARIETY

The present new variety of apricot tree was asexually reproduced by budding, as performed by us in our experimental orchard located near Modesto, Calif., which shows that all characteristics of the tree and its fruit run true to form and are established and transmitted through succeeding propagations.

SUMMARY OF THE VARIETY

A new and distinct variety of apricot tree which is of large size, semi-spreading in growth and is a regular and productive bearer of medium size, yellow flesh, freestone fruit with good flavor and eating quality. The tree is further characterized by producing early maturing fruit with firm flesh, which has the ability to be shipped to long distance markets and in comparison to Earlicot Apricot (U.S. Plant Pat. No. 7,198), the fruit of the new variety is approximately 5 to 6 days earlier in maturity.

BRIEF DESCRIPTION OF THE PHOTOGRAPH

The accompanying photograph shows reproductions in color of typical specimens of the fruit and foliage of our new variety of apricot tree. It depicts the upper and lower surface of the leaves, and an exterior and sectional view of the fruit divided in the suture plane to reveal flesh coloration, pit cavity and a stone remaining in place. The photograph was taken shortly after the fruit was picked (firm ripe) and the colors are as nearly true as is reasonably possible in a color representation of this type.

DESCRIPTION OF THE VARIETY

The following is a botanical detailed description of the new and distinct variety of apricot tree, its flowers, foliage and fruit, based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Form.*—Semi-spreading.
- *Shape.*—Usually pruned to vase shape.
- *Productivity.*—Productive.
- *Bearing.*—Regular.

Trunk:
- *Size.*—Large.
- *Texture.*—Shaggy.
- *Color.*—Brown to dark brown (6-F-5) to (6-F-7).

Branches:
- *Size.*—Medium to large.
- *Texture.*—Medium rough.
- *Lenticels.*—Numerous. Large size.
- *Color.*—New growth — reddish brown. Old growth — light brown to brown.

Leaves:
- *Size.*—Large. Average length 4¼". Average width 2¼".
- *Form.*—Ovate.
- *Texture.*—Smooth.
- *Margin.*—Serrate.
- *Thickness.*—Medium.
- *Petiole.*—Average length 1¼". Medium thickness.
- *Glands.*—Globose. Number varies from 0 to 4. Average number 2. Small size.
- *Color.*—Upper surface — green (28-F-7) to (28-F-8). Lower surface — dull green to green (28-E-5) to (28-E-6).

Flower buds:
- *Size.*—Medium to large.
- *Length.*—Medium.
- *Form.*—Plump.

Flowers:
- *Size.*—Large.

*Blooming period.*—Date of first bloom: Feb. 16, 1993. Date of full bloom: Feb. 24, 1993. Varies slightly with climatic conditions.

*Pollen.*—Present.

*Color.*—Light pink.

Fruit:

*Maturity when described.*—Firm ripe.

*Date of first picking.*—May 14, 1993.

*Date of last picking.*—May 20, 1993.

*Size.*—Medium. Average diameter axially 1¾" to 2". Average diameter in suture plane 1⅞" to 2". Average diameter measured at right angles to suture plane 1⅝" to 1⅞".

*Form.*—Nearly globose, slightly compressed in suture plane.

*Base.*—Retuse.

*Apex.*—Usually retuse, varies from retuse to rounded.

*Suture.*—Shallow, extends from base to apex.

*Ventral surface.*—Varies from rounded to slightly lipped.

*Cavity.*—Rounded to slightly elongated in suture plane. Average depth ¼". Average breadth ½".

Flesh:

*Ripens.*—Evenly.

*Texture.*—Firm.

*Amygdalin.*—Undetected.

*Juice.*—Moderate.

*Aroma.*—Moderate.

*Flavor.*—Good.

*Eating quality.*—Good.

*Color.*—Butter yellow to light orange (4-A-5) to (5-A-5).

Skin:

*Thickness.*—Medium.

*Texture.*—Medium — tenacious to flesh.

*Tendency to crack.*—Very slight.

*Down.*—Scant — very short.

*Color.*—Light yellow to pale orange (4-A-4) to (6-A-7). Varies with amount of exposure to direct sunlight.

Stone:

*Type.*—Freestone.

*Size.*—Medium. Average length ⅞" to 1". Average breadth ⅝" to ⅞". Average thickness 7/16" to ½".

*Form.*—Ovoid.

*Base.*—Straight.

*Apex.*—Nearly rounded, slight pistil point.

*Sides.*—Usually equal, varies from equal to unequal.

*Surface.*—Slightly pitted throughout.

*Ridges.*—Slight ridges extended across surface of the stone on both sides of suture.

*Tendency to split.*—Very slight.

*Color.*—Varies from golden brown to brown (5-D-5) to (5-E-5).

Use: Dessert.

*Market.*—Local and long distance.

Keeping quality: Good.

Shipping quality: Good.

The present new variety of apricot tree, its flowers, foliage and fruit, herein described may vary in slight detail due to climate, soil conditions and cultural practices under which the variety may be grown. The present description is that of the variety grown under the ecological conditions prevailing near Modesto, Calif.

We claim:

1. A new and distinct variety of apricot tree, substantially as illustrated and described, characterized by its large size, vigorous, semi-spreading growth and by being a productive and regular bearer of early maturing, medium size, yellow flesh, freestone apricots; the fruit is further characterized as having firm flesh with good flavor and eating quality, the ability to be shipped to long distance markets and in comparison to Earlicot Apricot (U.S. Plant Pat. No. 7,198), the fruit of the new variety is 5 to 6 days earlier in maturity.

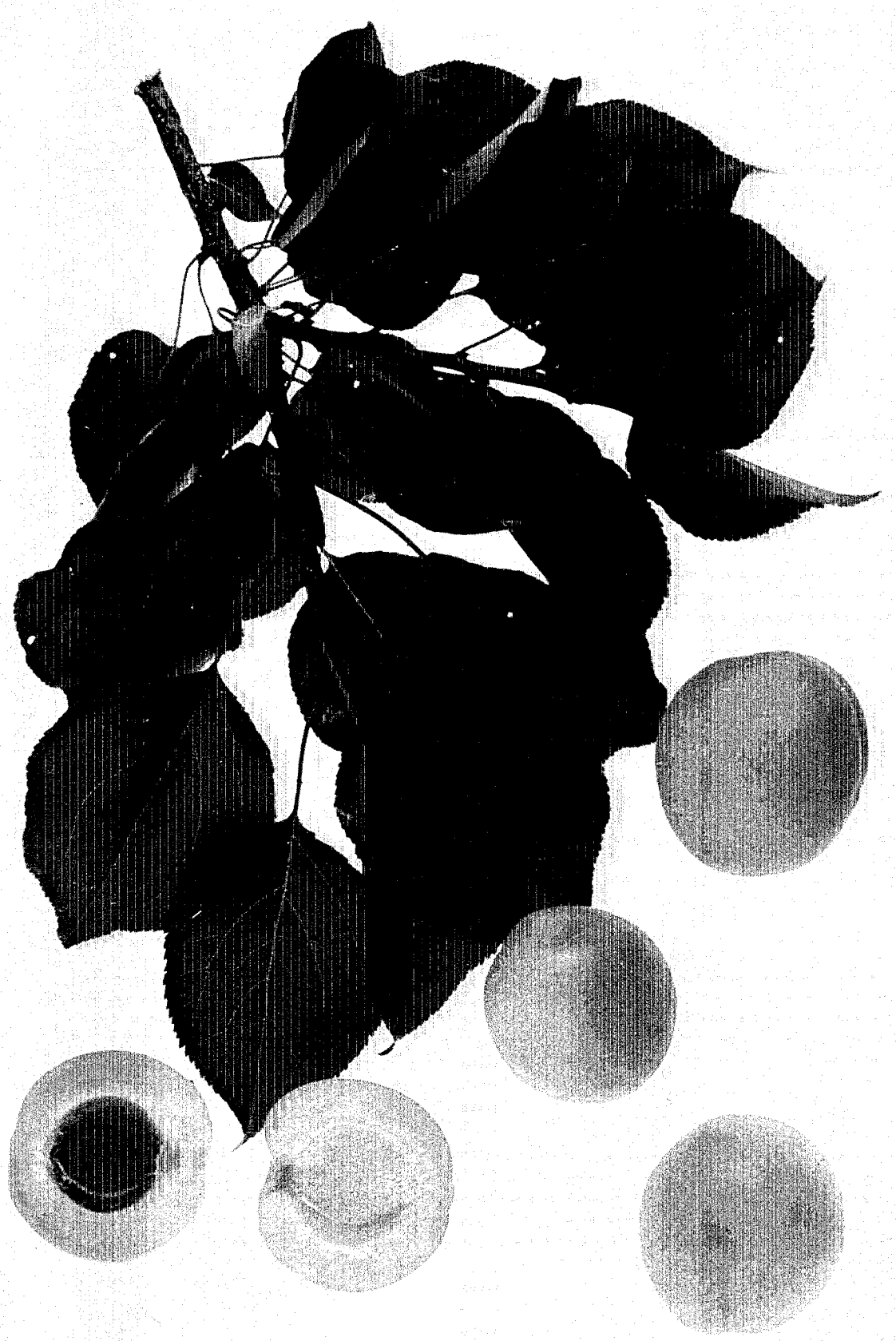

* * * * *